(12) United States Patent
Van Den Bossche et al.

(10) Patent No.: US 12,076,270 B2
(45) Date of Patent: Sep. 3, 2024

(54) WHOLE-BODY HYPERTHERMIA SYSTEM

(71) Applicant: ELMEDIX NV, Leuven (BE)

(72) Inventors: Johan Van Den Bossche, Linden (BE); Liesbet Conings, Linden (BE); Johannes Bogers, Boechout (BE)

(73) Assignee: ELMEDIX NV, Leuven (BE)

( * ) Notice: Subject to any disclaimer, the term of this patent is extended or adjusted under 35 U.S.C. 154(b) by 1528 days.

(21) Appl. No.: 16/345,920

(22) PCT Filed: Oct. 31, 2017

(86) PCT No.: PCT/EP2017/077932
§ 371 (c)(1),
(2) Date: Apr. 29, 2019

(87) PCT Pub. No.: WO2018/078188
PCT Pub. Date: May 3, 2018

(65) Prior Publication Data
US 2020/0046548 A1 Feb. 13, 2020

(30) Foreign Application Priority Data
Oct. 31, 2016 (GB) ..................................... 1618318
Mar. 10, 2017 (EP) ..................................... 17160450

(51) Int. Cl.
*A61F 7/00* (2006.01)
*A61F 7/12* (2006.01)
(Continued)

(52) U.S. Cl.
CPC .......... *A61F 7/0053* (2013.01); *A61F 7/0085* (2013.01); *A61F 7/12* (2013.01);
(Continued)

(58) Field of Classification Search
CPC .. A61F 7/0053; A61F 7/00; A61F 7/12; A61F 7/0085; A61F 2007/0054;
(Continued)

(56) References Cited

U.S. PATENT DOCUMENTS 3,840,019 A * 10/1974 Smirnov ................ A61F 7/0053
607/87
3,902,488 A * 9/1975 Sheppard .............. A61M 19/00
128/200.14
(Continued)

FOREIGN PATENT DOCUMENTS

CN 2160369 Y 4/1994
CN 1730108 A 2/2006
(Continued)

OTHER PUBLICATIONS

Cihoric et al., "Hyperthermia-Related Clinical Trials on Cancer Treatment Within the ClinicalTrials.gov Registry," International Journal of Hyperthermia, vol. 31, No. 6, 2015, pp. 609-614.
(Continued)

*Primary Examiner* — Margaret M Luarca
(74) *Attorney, Agent, or Firm* — Workman Nydegger (57) ABSTRACT

A whole-body hyperthermia system for raising the body temperature of the entire body of an individual to a predetermined target temperature and for stabilizing the body temperature at the target temperature comprises an apparatus means for raising the body temperature at a rate of at least 1° C./hour, and at least a second thermal means for further adjusting the body temperature to the target temperature Tb. The second thermal means comprises a fluid circuit, which is at least partially within the individual, and a fluid, heated by a heat exchanger to a set temperature is circulated through the fluid circuit.

10 Claims, 1 Drawing Sheet

(51) Int. Cl.
*A61M 5/44* (2006.01)
*A61M 16/10* (2006.01)
*A61N 5/06* (2006.01)

(52) U.S. Cl.
CPC ........ *A61M 5/445* (2013.01); *A61M 16/1005* (2014.02); *A61M 16/104* (2013.01); *A61M 16/1075* (2013.01); *A61N 5/0625* (2013.01); *A61F 2007/0002* (2013.01); *A61F 2007/0055* (2013.01); *A61F 2007/0057* (2013.01); *A61F 2007/006* (2013.01); *A61F 2007/0086* (2013.01); *A61F 2007/0096* (2013.01); *A61F 2007/126* (2013.01); *A61M 2205/3372* (2013.01); *A61M 2205/3606* (2013.01); *A61M 2205/362* (2013.01); *A61M 2210/0693* (2013.01); *A61M 2210/1064* (2013.01); *A61M 2210/1071* (2013.01); *A61M 2210/1082* (2013.01); *A61M 2230/50* (2013.01); *A61N 2005/0659* (2013.01)

(58) Field of Classification Search
CPC ...... A61F 2007/0018–0052; A61F 2007/0055; A61F 2007/006; A61F 7/0097; A61M 2205/3372; A61M 5/445; A61M 16/1075; A61M 2230/50; A61M 1/369; A61M 2205/366; A61N 5/0625; A61H 2201/02
See application file for complete search history.

(56) References Cited

U.S. PATENT DOCUMENTS

| | | | |
|---|---|---|---|
| 5,269,369 A * | 12/1993 | Faghri | A41D 13/0056 |
| | | | 607/104 |
| 5,292,347 A | 3/1994 | Pompei | |
| 6,156,007 A | 12/2000 | Ash | |
| 6,579,496 B1 | 6/2003 | Fausset et al. | |
| 7,403,704 B2 | 7/2008 | Eccleston et al. | |
| 7,666,213 B2 | 2/2010 | Freedman, Jr. et al. | |
| 8,613,762 B2 | 12/2013 | Bledsoe | |
| 8,668,065 B2 | 3/2014 | Kämpf et al. | |
| 8,834,404 B2 | 9/2014 | Beaudin | |
| 9,770,547 B2 | 9/2017 | Li | |
| 10,383,762 B2 | 8/2019 | Rapoport | |
| 2005/0021112 A1 | 1/2005 | Sakamoto | |
| 2005/0096714 A1 | 5/2005 | Freedman, Jr. et al. | |
| 2006/0030917 A1 | 2/2006 | Eccleston et al. | |
| 2008/0244637 A1* | 10/2008 | Candelore | H04N 21/44008 |
| | | | 725/28 |
| 2011/0036679 A1 | 2/2011 | Kämpf et al. | |
| 2011/0184253 A1* | 7/2011 | Archer | A61M 16/00 |
| | | | 128/202.16 |
| 2012/0029408 A1 | 2/2012 | Beaudin | |
| 2012/0158103 A1 | 6/2012 | Bledsoe | |
| 2016/0199241 A1 | 7/2016 | Rapoport | |
| 2016/0206471 A1 | 7/2016 | Rapoport | |
| 2016/0206493 A1 | 7/2016 | Rapoport | |
| 2017/0165409 A1 | 6/2017 | Li | |

FOREIGN PATENT DOCUMENTS

| | | |
|---|---|---|
| CN | 1897895 A | 1/2007 |
| CN | 101090684 A | 12/2007 |
| CN | 102781378 A | 11/2012 |
| CN | 103338730 A | 10/2013 |
| CN | 104667361 A | 6/2015 |
| CN | 204395086 U | 6/2015 |
| CN | 105722488 A | 6/2016 |
| CN | 105939695 A | 9/2016 |
| EP | 1581145 A2 | 10/2005 |
| EP | 2284413 A1 | 2/2011 |
| EP | 2320839 A2 | 5/2011 |
| EP | 2320839 A4 | 12/2011 |
| EP | 2401033 A1 | 1/2012 |
| EP | 3563814 A1 | 11/2019 |
| GB | 1352142 A | 5/1974 |
| JP | S5967947 A | 4/1984 |
| JP | H1033626 A | 2/1998 |
| JP | 2016531701 A | 10/2016 |
| WO | 2014196855 A1 | 12/2014 |
| WO | 2018078188 A1 | 5/2018 |

OTHER PUBLICATIONS

Van Der Zee, "Heating the Patient: A Promising Approach?," Annals of Oncology, vol. 13, 2002, pp. 1173-1184.
Worel et al., "Hepatic Dysfunction Contributes to Coagulation Disturbances in Patients Undergoing Whole Body Hyperthermia by use of Extracorporeal Circulation," International Journal of Artificial Organs, vol. 37, 2014, 12 Pages.
Extended European Search Report from EP Application No. 17160450.7, Sep. 21, 2017.
International Preliminary Report on Patentability from PCT Application No. PCT/EP2017/077932, Feb. 15, 2019.
Partial International Search Report and Written Opinion from PCT Application No. PCT/EP2017/077932, Feb. 1, 2018.
International Search Report and Written Opinion from PCT Application No. PCT/EP2017/077932, Apr. 17, 2018.
Written Opinion from PCT Application No. PCT/EP2017/077932, Nov. 30, 2018.
Written Opinion of corresponding PCT Application No. PCT/EP2019/061317, Mar. 17, 2020.
Office Action from corresponding CN Application No. 201780067433.0, Dec. 3, 2020.
Chinese Office Action from corresponding CN Application No. 201780067433.0, Jul. 7, 2021.
European Search Report from EP Application No. EP19201493, Feb. 10, 2020.

* cited by examiner

WHOLE-BODY HYPERTHERMIA SYSTEM

TECHNICAL FIELD

The present invention relates to a whole-body hyperthermia system for raising the body temperature of an individual to a predetermined target temperature $T_b$ and for stabilizing the body temperature at the target temperature $T_b$. The present invention further relates to a method for subjecting a patient to a whole-body hyperthermia condition and to an anti-tumour compound for use in the treatment of e.g. cancer.

BACKGROUND ART

Cancer therapies aim to maximally remove tumour tissue while preserving healthy tissue as much as possible. However, surgery and irradiation are locally applied, and a small amount of cancer cells which are at remote positions from the site of intervention are not detected or removed. Equally, chemotherapy often does not kill all tumour cells.

Consequently, alternative anti-tumour therapies are needed.

It has been described that tumour cells are sensitive for stress conditions, such as elevated temperatures. Indeed, treatment at temperatures between 40 and 44° C. is cytotoxic for cells in an environment with a low pO(2) and low pH, conditions that are found specifically within tumour tissue, due to insufficient blood perfusion. Under such conditions radiotherapy is less effective, and systemically applied cytotoxic agents will reach such areas in lower concentrations than in well perfused areas. Therefore, the addition of hyperthermia to radiotherapy or chemotherapy will result in at least an additive effect. Furthermore, the effects of both radiotherapy and many drugs are enhanced at an increased temperature. Hyperthermia can be applied by several methods: local hyperthermia by external or internal energy sources, regional hyperthermia by perfusion of organs or limbs, or by irrigation of body cavities, and whole-body hyperthermia. [reviewed in van der Zee (2002) *Ann. Oncol.* 13, 1173-1184; Heating the patient: a promising approach?].

Cihoric N et al. (2015) Int J Hyperthermia 31, 609-614 "Hyperthermia-related clinical trials on cancer treatment within the ClinicalTrials.gov registry." gives an overview of 109 clinical trials in which hyperthermia was part of the treatment regimen. 12 of these were performed with whole body hyperthermia. Devices and methods to apply local hyperthermia have been described in EP2401033, EP2284413, EP1581145.

Worel et al. (2014) *Int. J Artif. Organs.* 37, 1-12 describe methods and devices to apply whole body hyperthermia on cancer patients under moderate sedation enabling spontaneous breathing.

JP H10 33626 describes an apparatus for the treatment of cancer and AIDS, by use of whole-body hyperthermia. U.S. Pat. No. 6,579,496 describes a method for hyperthermia, including extracorporeal blood heating and sorbent-based detoxification.

Elevated temperatures, mimicking severe near-lethal fever, are difficult to apply in a "whole-body" approach, especially for prolonged periods (e.g. more than 6 hours). This is in part due to the fact that it is difficult to obtain a homogenous, or uniform, elevated temperature of treatment in the body, with the additional complication that specific body parts may have to be maintained at a lower temperature than the treatment temperature in order to prevent functional damage to the body part.

Methods and devices allowing a long term whole body hyperthermia with maximal safety, minimal discomfort and high efficacy are lacking.

SUMMARY OF THE INVENTION

The methods and devices of the present invention has the advantages that whole body hyperthermia can be applied for much longer time periods than used in the prior art.

Prior art methods are applied on patients for short periods because of the discomfort of the patient which is at most moderately sedated. The methods and devices of the present invention allow to compensate for the discomfort that occurs when the whole body temperature is applied for more than 4 h, more than 6 h, or more than 12 h.

The methods of the present invention have the advantage that tumour cells are challenged for a much longer time and that tumour cells death occurs more efficient compared to shorter treatments.

The methods of the present invention avoid the selection of heat-resistant tumour cells as may occur with repetitive exposure to hyperthermic conditions for shorter time periods. Indeed, sub-optimal conditions as used in the prior art may select those cells with superior heat shock protein repair systems, making the cells resistant for further hyperthermic conditions. With the methods of the present invention, the risk of selecting heat resistant cells is dramatically reduced.

This consequently allows repeating long term hypothermic treatments, especially in combination with chemotherapy. Indeed, high temperatures improve the uptake of anti-cancer drugs allowing the use of lower doses of medicaments, and consequently fewer side effects. The methods of the present invention allow repetitive treatments of long term hyperthermia combined with chemotherapy at reduced dosages. In combination treatment the chemotherapeutic can be applied before, during or after the hyperthermia treatment.

The present invention has the advantage that heat loss from the body is reduced and kept to its minimum. When extracorporeal heating devices are used, the temperature at the heating device can be kept close to the target temperature to be achieved at the body. Prior art methods and devices wherein an individual is wrapped in blanket loose substantial heat via the skin, or via breathing, such that the heating devices of the patient have to compensate the heat loss by heating the blood to temperatures above the target temperature of the body.

The different measures for minimising the loss of heat from the body have the advantages that the excess of heat that has to be applied to the body is as low as possible. This in contrast with the prior art systems with extracorporeal blood heating wherein the blood needs to be heated to substantially higher temperatures than the target temperature to compensate for loss of e.g. heat by respiration, or inadequate isolation of the body.

One aspect of the invention relates to whole-body hyperthermia systems for raising the body temperature of the entire body of an individual to a predetermined target temperature $T_b$ and for stabilizing the body temperature at the target temperature $T_b$, systems comprising: a cabinet with isolation and heating for maintaining an individual at an elevated temperature, at least one thermal means for raising and stabilising the temperature of the individual, one or more devices to prevent or counter heat loss from the individual, one or more sensors monitoring the temperature or heat flux of the individual, connected to controllers steering the devices to prevent or counter heat loss and steering the at least one thermal means.

For the purpose of the present invention, the term "cabinet" refers to a confined space wherein the patient is located for the hyperthermal treatment.

According to certain embodiments, the cabinet may be a sarcophagus-shaped space. Alternatively, it may be formed of panels, preferably, from a fabric with heat-isolating properties, which may further take the form of a tent, surrounding the patient. Typically, the cabinet refers to the room, or a heat-sealed, confined part of a room, wherein the patient is located during treatment. When the patient is placed in a bath with fluid, use is made of a larger cabinet for harbouring the bath. The cabinet is provided with isolation to prevent the outflow of heat from the cabinet, and with heating for heating the air of the cabinet. Said isolation has thus the purpose of reducing heat losses and heat fluxes from the body to its surroundings, as well as from the cabinet to its surroundings to a minimum, ideally to zero. Under these conditions, no thermal energy escapes from the body. As such, the cabinet has the purpose of maintaining an individual at an elevated temperature.

At the end of the treatment, the isolating function can advantageously at least partially be removed, e.g. by creating a current of cooler air, in order to cool the body's temperature.

The air in the cabinet, surrounding the patient, is in other words fully controlled, in terms of temperature, but also in terms of humidity. Indeed, the cabinet is preferably provided with means for creating an environment at a desired temperature and humidity, with the aim of preventing dehydration of the patient.

Herein the devices to prevent or counter heat loss are typically devices for heating air and/or oxygen for respiration, or devices for heating liquids being introduced in the body. Preferably, such devices further also administer said heated air and/or oxygen, or heated liquids to the body.

It is an advantage of such devices heating air and/or oxygen for respiration, that the heat-exchange capabilities of the lungs can be used. The inventors have found that the temperature at which air and/or oxygen for respiration is administered, has a significant influence of the uniformity and safety of heating the body and can substantively support the hyperthermia treatment. Typically, in order to use the lungs for the exchange of heat, the patient is brought under general anaesthesia.

Advantageously, the air and/or oxygen that is heated, and administered to the body, has a humidity level that is in service of preventing dehydration of the body.

According to preferred embodiments, an inhalation mask is used to provide the lungs with heated and humidified air (0-100%). This allows to apply a different temperature to the lungs compared with the rest of the body.

For the purpose of the present invention, the term "at least one thermal means" refers to means that are configured to provide a fast heating, more in particular by raising said body temperature at a rate of at least 1° C./hour, and subsequently set to obtain and maintain the target temperature.

The at least one thermal means typically comprise first thermal means, which are provided for raising the body temperature at a rate of at least 1° C./hour, and second thermal means for further adjusting the body temperature to the target temperature Tb.

In embodiments of these systems the sensor monitoring the temperature of the individual are sensors measuring the temperature internally, sensors measuring the temperature externally and contacting the skin, or sensors measuring the temperature externally and not contacting the skin.

In embodiments of these systems, the sensor monitoring the temperature of the individual are one or more heat flux sensors attached to the skin of the individual.

Preferably, the sensors are interconnected by use of a network, wherein a sensor controller monitors, preferably continuously, the outcome of the individual sensors and steers the heating and/or cooling of the whole body, specific body parts and/or individual organs. It is an advantage of such a network and a controller steering temperature at local level, that hotspots in the body, potentially due to increased exothermic activity of organs, can be avoided.

According to embodiments of the present invention, the system can monitor and control all heat fluxes to and from the body and therefore the temperature of all body parts, using a combination of the sensor measurements and the specifications of the cabinet, the at least one thermal means and the devices to prevent or counter heat loss.

Embodiments of these systems, comprise a first thermal means for raising the body temperature at a rate of at least 1° C./hour, and at least a second thermal means for further adjusting the body temperature to the target temperature $T_b$, wherein the second thermal means comprise a fluid circuit, which is at least partially within the individual, wherein a fluid, heated by a heat exchanger to a set temperature $T_f$, is circulated through the fluid circuit.

In embodiments of these systems, the first and the second means are different from each other.

In embodiments of these systems, the fluid circuit is an internally heated fluid circuit.

In embodiments of these systems the fluid circuit is an internally heated catheter.

In embodiments of these systems, the first thermal means comprises a pump selected from the group consisting of a roller pump, a centrifugal pump, a pulsatile pump and a non-occlusive roller pump.

In embodiments of these systems, the system is provided with means for monitoring the body temperature and/or vital signs of the individual, such as respiratory activity, and/or cardiac activity and blood parameters.

In embodiments of these systems, the means for monitoring the body temperature is a heat sensitive camera measuring the temperature of a part of the skin of the body.

In embodiments of these systems, the means for monitoring the body temperature comprise at least one temperature probe for monitoring at least one temperature signal at at least one location on or within the individual; and means for deriving an overall value, being the monitored body temperature $T_m$, from the at least one temperature signal.

In embodiments of these systems, a controller uses at least the monitored body temperature $T_m$ for generating a control signal for the first and second thermal means for steering $T_m$ to the target temperature $T_b$. As explained for embodiments hereabove, the outcome of at least one temperature sensor or probe is used for deriving an overall value, which is used for steering the heating and/or cooling of the whole body, body parts and/or individual organs.

In embodiments of these systems the system is provided with means for maintaining the monitored body temperature $T_m$ within a range of at most 0.5° C. from the predetermined target temperature $T_b$.

Typically, said monitored body temperature Tm represents an overall value that is representative for the temperature stage the heated body temperature can be situated in during the treatment. It therefore has the purpose of serving as an indication for the system to further steer heating (or cooling) of the body. As explained hereabove, the system is preferably also provided with means to maintain specific body parts at a particular, preferably lower, temperature.

In embodiments of these systems, the system is provided with means to bring the individual under sedation or complete narcosis, and with means to supply oxygen to the individual, wherein the oxygen supplying means are provided to supply oxygen to the individual at a temperature $T_b$. Said oxygen supplying means can be part of the devices for heating air and/or oxygen for respiration. Advantageously, the temperature as well as the humidity of the administered air and/or oxygen can be adapted to the heating or cooling needs of the patient.

In embodiments of these systems, the first and second thermal means are provided for raising the body temperature to the target temperature $T_b$ for maintaining $T_b$ at least a period of time $t_p$, wherein the period of time $t_p$ is at least 6 hours, at least 8 hours or at least 12 hours.

In embodiments of these systems, the system is provided with means to administer additional compounds to the individual, such as transfused blood, chemotherapeutic drugs and/or nutritional compounds, such as salt solutions, and wherein the additional compounds are administered at a temperature $T_b$. Advantageously, the temperature of the additional compounds can be adapted to the heating or cooling needs of the patient.

In embodiments of these systems, the system is provided with one or more isolation elements for an individual, such as isolation foil or suit for torso or limbs, or a helmet or cap like device for application on the head.

In embodiments of these systems the first thermal means has at least a first portion and at least a second portion, wherein the at least first portion of the first thermal means is arranged to raise the body temperature of at least a first series of body parts of the individual to the target temperature $T_b$, and wherein the at least second portion of the first thermal means is arranged to prevent at least a second series of body parts to exceed a target temperature $T_s$, wherein the temperature $T_s$ is lower than the temperature $T_b$.

Another aspect of the invention relates to disposable kits for use in the above systems, comprising tubing for a fluid circuit for blood supply to an individual and comprising sensors to monitor the temperature or heat loss from the patient.

Such kits may further comprise an isolation element for an individual, such as isolation foil or suit for torso or limbs, or a helmet or cap like device for application on the head.

Such disposable kits may further comprise means for cooling selected parts of the individual's body, said parts being typically individual organs, with the purpose of keeping the organ's temperature at a constant, uniform temperature, which is preferably lower than the target temperature Tb that is desired for the rest of the body.

Organs for which such a different, preferably lower temperature may be targeted include the brain, the liver, the kidneys and the colon.

Said means for cooling individual organs can be provided on the skin of the individual, nearby the location of the organ, providing cooling through the skin. Alternatively, said means for cooling individual organs may be applied on the surface of the organ itself, typically by use of minimally invasive or keyhole surgery.

Another aspect of the invention relates to methods for subjecting an individual to a whole-body hyperthermia condition using a whole-body hyperthermia system as described above, the method comprising the steps of placing the individual in a heated cabinet;
applying means for monitoring the body temperature;
deriving from the monitoring of the body temperature an overall value, being the monitored body temperature $T_m$;
generating a control signal from the monitored body temperature $T_m$ for thermal means, for steering $T_m$ to the target temperature $T_b$;
whereby the individual is kept in hyperthermia condition for at least 6 hours, or at least 8 hours, or at least 12 hours, during which period the monitored body temperature $T_m$ of the patient does not deviate by more than 0.5° C., or 1.0° C. from the predetermined target temperature $T_b$.

In embodiments of these methods, heat losses from the individual are compensated by one or more of the following steps:
heating the skin of the individual or parts thereof by controlling the temperature of the air surrounding the individual;
applying isolation on one or more parts of the body;
heating air used for respiration to a controlled temperature;
heating liquids for administering, nutrients, moisture or medicaments to a controlled temperature.

In embodiments of these methods, the first and second thermal means are used which differ from each other.

In embodiments of these methods, the individual is kept in hyperthermia condition at a temperature between 40 and 42° C.

In embodiments of these methods, wherein the individual is kept in hyperthermia condition for at least 12 hours.

In typical embodiment of these methods, the individual is a cancer patient.

In typical embodiment of these method, the individual is under complete narcosis.

Another aspect relates to the use of a kit in accordance as described above, in a method as described before.

Another aspect relates to an antitumor compound for use in the treatment of cancer, wherein the compound is administered to a patient which is under a whole body hyperthermia of between 41.5° C. and 42.0° C. for at least 6 h.

One aspect of the invention relates to whole-body hyperthermia systems for raising the body temperature of the entire body of an individual to a predetermined target temperature $T_b$ and for stabilizing the body temperature at the target temperature $T_b$, comprising an apparatus having a first thermal means for raising the body temperature at a rate of at least 1° C./hour, and at least a second thermal means for further adjusting the body temperature to the target temperature $T_b$, wherein the second thermal means comprise a fluid circuit, which is at least partially within the individual, wherein a fluid, heated by a heat exchanger to a set temperature $T_f$, is circulated through the fluid circuit.

In embodiments thereof, the first and the second means are different from each other.

In embodiments thereof, the first and the second means are the same.

In embodiments thereof, the fluid circuit is an internally heated fluid circuit, typically an internally heated catheter.

In embodiments thereof first thermal means comprise a pump selected from the group consisting of a roller pump, a centrifugal pump, a pulsatile pump and a non-occlusive roller pump.

In embodiments thereof the systems are provided with means for monitoring the body temperature and/or vital signs of the individual, such as respiratory activity and/or cardiac activity.

In embodiments thereof means for monitoring the body temperature is a heat sensitive camera measuring the temperature of a part of the skin of the body.

In embodiments thereof, means for monitoring the body temperature comprise at least one temperature probe for monitoring at least one temperature signal at at least one location on or within the individual; and means for deriving an overall value, being the monitored body temperature $T_m$, from the at least one temperature signal.

The monitoring of the body temperature refers to thermometers measuring the temperature (internal, external, remote, heat map) or flux sensors measure the heat loss using applied on the body. Flux sensors have the advantages that the flux is determined over the entire surface of the sensor and provide a more accurate measurement than local temperature determination of a thermometer.

In embodiments thereof, a controller uses at least the monitored body temperature $T_m$ for generating a control signal for the first and second thermal means for steering $T_m$ to the target temperature $T_b$.

In embodiments thereof, the system is provided with means for maintaining the monitored body temperature $T_m$ within a range of at most 0.5° C., preferably at most 0.1° C. from the predetermined target temperature $T_b$.

In embodiments thereof, the system is provided with means to bring the individual under sedation, and with means to supply oxygen to the individual, wherein the oxygen supplying means are provided to supply oxygen to the individual at a temperature $T_b$.

In embodiments thereof, first and second thermal means are provided for raising the body temperature to the target temperature $T_b$ for at least a period of time $t_p$, wherein the period of time $t_p$ is at least 6 hours, at least 8 hours or at least 12 hours.

In embodiments thereof the system is provided with means to administer additional compounds to the individual, such as transfused blood, chemotherapeutic drugs and/or nutritional compounds, such as salt solutions, and wherein the additional compounds are administered at a temperature $T_b$.

In embodiments thereof the first thermal means has at least a first portion and at least a second portion, wherein the at least first portion of the first thermal means is arranged to raise the body temperature of at least a first series of body parts of the individual to the target temperature $T_b$, and wherein the at least second portion of the first thermal means is arranged to prevent at least a second series of body parts to exceed a target temperature $T_s$, wherein the temperature $T_s$ is lower than the temperature $T_b$. Said second portion can include means for cooling individual organs.

Another aspect of the invention relates to, methods for subjecting an individual to a whole-body hyperthermia condition using a whole-body hyperthermia system as described above, the comprising the steps of
applying means for monitoring the body temperature and/or vital signs of the individual;
deriving from the monitoring of the body temperature an overall value, being the monitored body temperature $T_m$;
generating a control signal from the monitored body temperature $T_m$ for a first and second thermal means, for steering Tm to the target temperature $T_b$;
raising the body temperature of the patient at a rate of at least 1° C./hour using the first thermal means; and
adjusting the patient's body temperature to the target temperature $T_b$ using the second thermal means,
wherein the individual is kept in hyperthermia condition for at least 6 hours, or at least 8 hours, or at least 12 hours, during which period the monitored body temperature $T_m$ of the patient does not deviate by more than 0.5° C. from the predetermined target temperature $T_b$.

In embodiments thereof the first and the second means differ from each other.

In embodiments thereof, the individual is kept in hyperthermia condition at a temperature between 40 and 42° C.

In embodiments thereof, the individual is kept in hyperthermia condition for at least 12 hours.

In embodiments thereof, the individual is a cancer patient.

Another aspect of the invention are antitumor compounds for use in the treatment of cancer, wherein the compound is administered to a patient which is under a whole body hyperthermia of between 41.5° C. and 42.0° C. for at least 2 h.

The methods and devices of the present invention have the advantage that a whole body hyperthermia can be applied for a prolonged period and at narrowly controlled temperatures.

Similar to the external heating of blood via perfusion systems, embodiments of the present invention which rely on catheters take advantage of the blood stream of the individual to transport the heated blood throughout the entire body, including tissues and organs at the interior of the individual.

Embodiments of methods and devices of the present invention which use perfusions systems or the like have the advantage that a whole body hyperthermia can be obtained without physical damage to blood cells and organelles cause by peristaltic pumps. Indeed, prior art methods which rely on externally heating the blood require typically peristaltic pumps which damage blood cells and organelles.

In the methods and devices of the present invention, pumps such as a roller pump, a centrifugal pump, a pulsatile pump and a non-occlusive roller pump can be used for circulating blood with significantly less damage compared to a peristaltic pump.

In the present invention the combination of the external heating and the internal heating allow to bring the patient in a short time period to the desired temperature in the entire body without a risk of local overheating. Furthermore, the heating of the blood in combination with other means provides a homogeneous heating in the body (such as temperature controlled air supply, nutrient supply, ambient temperature, heat flux sensors). Monitoring of the temperature by e.g. internal temperate probes or heat sensitive cameras), allows to adjust the heat supply of a heating system.

For the purpose of the invention, the term "homogeneous heating" refers to a process of heating the human body, said heating being uniform in character. As such, the body or body parts that are being heated in a homogeneous way typically have a temperature during the hyperthermal treatment that does not deviate more than 0.5° C., preferably not more than 0.4° C., more preferably not more than 0.3° C., even more preferably not more 0.2° C. and most preferably not more than 0.1° C., from the average of the temperatures measured in the body or body parts.

Heating the body or body parts in a uniform way allows to accurately monitor and control the hyperthermal treatment of the body. Accurate monitoring means in this context that the user of the system not only disposes of a set of sufficiently precise temperature measurements, but preferably also of a spatial image of a possible temperature distribution of the body. The advantage herein is that the hyperthermal treatment can be performed in a safe manner, wherein local body temperatures in all parts of the body remain below certain threshold values.

DETAILED DESCRIPTION OF THE INVENTION

Figure 1:
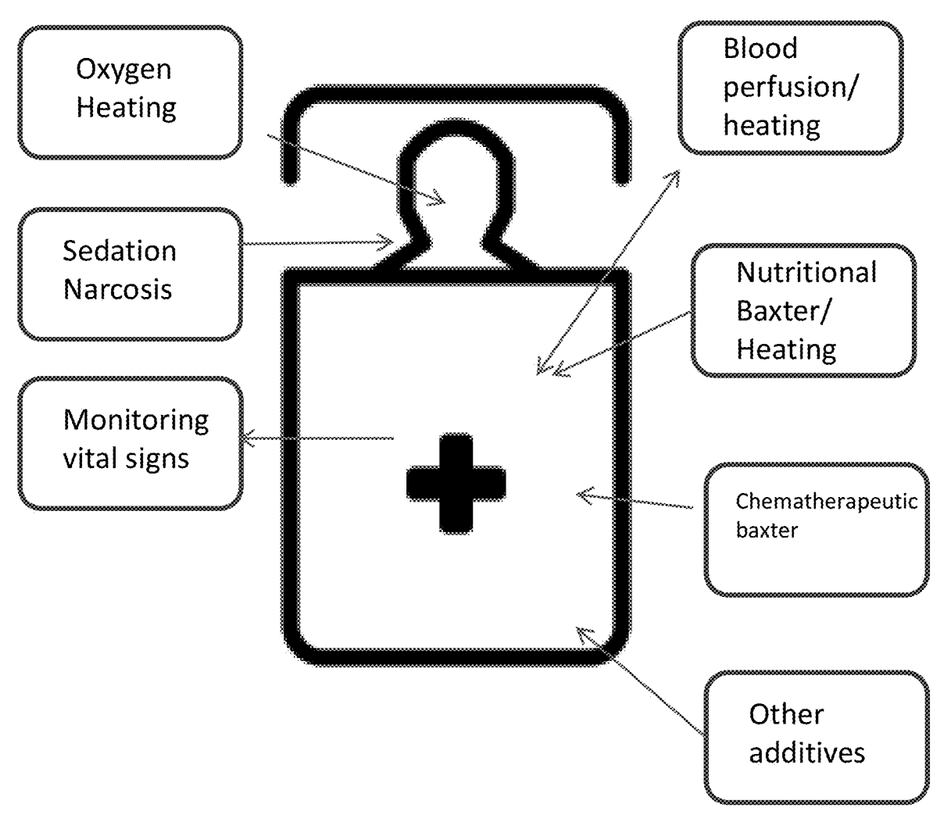
FIG. 1 is a schematic illustration of the system according to the present invention.

It is established that the temperature of the human body can be increased up to a temperature of 43° C. for a longer period without any adverse effects. However, some body parts cannot exceed this temperature. As a consequence, temperature $T_b$ is in the range of 40.5° C. to 43° C., preferably in the range of 41° C. to 42.5° C., more preferably in the range of 41.5° C. to 42.0 C°. It is further understood that good results can be obtained when $T_b$ is around 41.5° C.

The whole-body hyperthermia system comprises typically a first thermal means and a second thermal means for the heating of the blood by extracorporeal or internal devices. The invention is further described with emphasis on those embodiments wherein two different thermal means are used. Nevertheless, as cited below, one single thermal means can be used in alternative embodiments.

The first thermal means are arranged for raising the patient's body temperature at a rate of at least 1° C./hr, preferably at a rate of at least 2° C./h, more preferably at a rate of at least 3° C./h, even more preferably at a rate of at least 4° C./h, more preferably at a rate of at least 5° C./h, even more preferably at a rate of at least 6° C./h and most preferably at a rate of at least 7° C./h.

As mentioned herein above, some vulnerable body parts of the human body cannot be exposed to a temperature which exceeds a certain threshold value. For example, the temperature of the brain cannot exceed 43° C. as brain damage could occur.

Brain functioning can even be damaged at a lower temperature. Preferably, the temperature of the brain is kept at 41.8° C. or below, preferably at around 41.5° C. or more preferably at around 41° C.

Other body parts that cannot be exposed to an overall body temperature of 43° C. include the liver, the kidneys and the colon.

According to embodiments of the invention, these body parts are kept at the same temperature as the brain in order to avoid damage, the temperature being 41.8° C. or below, preferably 41.5° or more preferably 41° C.

First thermal means are generally provided with at least a first portion for heating a first series of body parts of the patient to the target temperature $T_b$ and at least a second portion for preventing a second series of body parts of the patient of exceeding a temperature $T_s$, which is lower than $T_b$.

Preferably, $T_s$ is not higher than 41.0° C.

Hence, by avoiding the more vulnerable body parts, such as the brain, to exceed the temperature $T_s$, tissue damage of the vulnerable body parts can be avoided, while other body parts, such as the torso are allowed to be heated to the target temperature $T_b$.

In specific embodiments the head, or a part thereof is kept as a precaution at a lower temperature (e.g.) 0.5° C., 1° C., 2° C. than the remainder of the body under hyperthermic condition, using e.g. a helmet with cooling or a gel containing blanket with cooling. In addition, pressure sensors can be provided to measure excess pressure in the skull which is indicative for overheating of the brain and subsequent brain damage.

It is understood that temperature control of all body parts at all times is a crucial aspect for hyperthermia treatment, so that upon heating, vulnerable body parts do not exceed a certain threshold temperature. It is understood that the first series of body parts and the second series of body parts do not overlap.

The methods and apparatus of the present invention envisages that the temperature of the body is initially raised to 42, or 42.5 or 43° C. for a period of about 15, 30, 45 or 60 minutes and afterwards kept at the desired target temperature of target temperature.

Equally, a local heating above the target temperature can be applied at a region of the body comprising a tumour. Such heating makes the tissue more vulnerable for a subsequent treatment such as local irradiation.

Typically, first thermal means may include a thermal bath, or a garment. A thermal bath may be divided in two parts, wherein a first part is arranged for heating the first series of body parts to the target temperature $T_b$, and a second part which is arranged for preventing the second series of body parts to exceed the lower temperature $T_s$. In order to raise the patient's body temperature, the bath may be filled with a substance such as heated water or molten wax. Alternatively, a garment may be carried by the patient or wrapped around the patient's body, and typically comprises a fluid circuit that provides a flow of heated fluid around the body.

According to one embodiment, the patient's body temperature is raised to the predetermined target temperature $T_b$ by using heat radiation. For this purpose, the patient can be placed in a confined space, which may comprise isolating means for secluding the second series of body parts from overheating. Typically, the heat radiation means make use of infrared A radiation.

According to a preferred embodiment, the patient's body temperature is raised to the predetermined target temperature $T_b$ making use of a closed loop fluid circuit.

Preferably, a so-called internally heated fluid circuit ("internally heated fluid circuit", herein after) can be used, wherein the internally heated fluid circuit can comprise a flexible catheter, which is inserted into a blood vessel through the vascular system of the patient and wherein a fluid is circulated. The catheter further comprises a heat-transfer element which is positioned in the blood vessel, thus enabling the transfer of heat between the blood and the fluid of the fluid circuit. The fluid is pumped through the catheter of the closed circuit.

Alternatively, use can be made of a so-called externally heated fluid circuit ("externally heated fluid circuit", herein after) wherein blood is withdrawn from the human body in a continuous mode, and wherein the blood is circulated in a continuous flow partially outside of the human body. The blood is heated outside of the human body in a heat-exchanger and subsequently returned to the body by a pump. As a consequence, the blood circulatory system of the human body is part of the closed loop fluid circuit.

Advantageously, blood temperature measurements during the procedure can be used as a measure for the stability of the procedure, with the purpose of detecting active internal heat sources.

In specific embodiments the natural breathing of an individual can be replaced by external devices. Alternatively, oxygen is supplied to the blood via the extracorporeal blood circulation devices.

Advantage and Shortcomings
First Thermal Means

Advantageously, the first thermal means allow for a rapid, controlled heating of the patient's natural body temperature to a higher temperature. A rapid controlled heating has as an advantage that the overall treatment will take less time. This is both in the economic interest of the healthcare provider as advantageous for the comfort of the patient.

However, the first thermal means, arranged for providing a fast heating of the body temperature, would have to be adjusted quite early in the heating process in order to avoid overshooting of the target temperature $T_b$. It must be remembered that exceeding a threshold temperature has to be avoided at all times, due to the risk of causing permanent damage to vulnerable body parts and organs such as the brain. As a result, the patient's body temperature, although raised at a high speed in the beginning of the treatment, would only converge slowly to the target temperature $T_b$.

Overshooting can be avoided by providing PID controllers wherein the controller allows an initial fast heating and is stepwise adjusted to provide a slower heating followed by a steady state control to correct minor variations.

According to one embodiment of the present invention, the first thermal means are arranged for providing a fast heating of the patient's own body temperature to a temperature $T_b$-X, at a rate as determined here above. X is in the range of 0.2° C. to 2° C., preferably in the range of 0.4° C. to 1.6° C., more preferably in the range of 0.6° C. to 1.2° C.

Fast heating by the first thermal means of the patient is typically performed by external heating of the blood system, and optionally combined with heating by a catheter. Alternatively, said first thermal means comprise an internally heated fluid circuit.

Heat loss occurs via breathing and mainly via the skin. The fast heating is thus generally combined with means such as isolating blankets or gel packs, warm water baths, heated cabinets and the like. Also blankets and gel packs can be connected to a water supply to maintain the skin moist and thereby preventing dehydration.

Air used for respiration can be heated or alternatively by long term anaesthetics, the lung function is interrupted and oxygen supply to the blood is provided via an external blood circuit.

Second Thermal Means

The apparatus of the whole-body hyperthermia treatment system according to the present invention further comprises a second thermal means, wherein the second thermal means comprise a fluid circuit which is at least partially within the patient, wherein a fluid, heated by a heat exchanger to a set temperature $T_f$, is circulated through the fluid circuit.

The temperature $T_f$ is in the range of $T_b$+/−0.5° C. Preferably, the temperature $T_f$ is equal to $T_b$.

According to one embodiment of the present invention, the fluid circuit is an externally heated fluid circuit, wherein the fluid is the blood of the patient and the patient's blood circulatory system is part of the fluid circuit. Part of the patient's blood is removed from the body, then heated by a heat-exchanger, external to the body, and subsequently returned to the body, where the heated blood is circulated further through the patient's body. This external circuit allows the adjust the oxygen content of the blood.

In a preferred embodiment according to the present invention, the fluid circuit is an internally heated fluid circuit, comprising a catheter wherein a heating fluid is circulated. The catheter is introduced in a blood vessel of the patient's body and a fluid is circulated through the catheter. The catheter further comprises a heat exchanger which is arranged for exchanging heat between the heating fluid and the patient's blood. The heating fluid is heated outside of the body in a heat exchanger. The heating fluid is typically circulated through the fluid by a pumping device.

Typically, the pumping device is a peristaltic pump, for heating during limited time periods. Perfusion pumps are used as an alternative since they cause less physical damage to the blood cells.

It has now been found that the combination of the first and second thermal means allow for effective heating of the patient's body.

Once a desired temperature is obtained using the first means, the first means is switched of and subsequent heating is performed by the second means. Alternatively or in addition, the heating by first means is lowered by lowering the heating or lowering the flow rate of heated blood from an external blood circuit.

In one embodiment according to the present invention, the whole-body hyperthermia system is further provided with means for monitoring the patient's body temperature and/or vital signs. The means for measuring vital signs include means for measuring the respiratory activity, if respiration is maintained, as well means for measuring the cardiac activity of the patient while under hyperthermia treatment.

The temperature of the patient, as well as the vital signs, are monitored using procedures well known in the art.

In one embodiment, the means for measuring the body temperature of the patient comprise at least one single temperature probe for monitoring at least one single temperature signal at at least one location on or within the patient.

In a preferred embodiment, the means for measuring the body temperature comprise at least two temperature probes. Preferably, at least one means for measuring the body temperature is located on the skin of the patient, thereby measuring the temperature of the skin of the patient, and at least one is located on a body part of the patient, other than the skin.

A further means for measuring the body temperature comprises a heat sensitive camera, which can measure the temperature of a significant surface of the skin.

In a more preferred embodiment according to the present invention, the means for monitoring the patient's body temperature comprise a plurality of temperature probes, which generate a plurality of temperature signals. Preferably, the temperature signals are measured in a continuous mode.

The whole-body hyperthermia system further comprises means for deriving, preferably in a continuous mode, from the at least one temperature signal an overall value, which is the monitored body temperature $T_m$. The measured body temperature $T_m$ equals the one single temperature signal, when only one single temperature probe is used. When at least two temperatures probes are used, the measured body temperature is calculated from the at least two temperature signals.

The monitored body temperature $T_m$ is derived from the at least two temperature signals according to procedures well known in the art.

The monitored body temperature $T_m$ is derived in such a way that the optimal condition for hyperthermia treatment of the patient is considered to be achieved, when $T_m$ is equal or close to the predetermined target temperature $T_b$.

It is hereby understood that the monitored body temperature $T_m$ is considered equal or close to the predetermined target temperature $T_b$, when $T_m$ is within the range of at most 0.5° C., preferably of at most 0.4° C., more preferably of at most 0.3° C., even more preferably of at most 0.2° C. and most preferably of most 0.1° C. from the predetermined target temperature $T_b$.

In one embodiment according to the present invention, the whole-body hyperthermia system comprises a controller. The controller is arranged to use the measured body temperature $T_m$ as an input signal for generating a control signal to steer the first and second thermal means, allowing thereby $T_m$ to approach $T_b$ and stabilize at this temperature.

For the purpose of the present invention, the above described first means and second means are typically different. In specific embodiments the first and second means can be the same, whereby one heating means is initially set to provide a fast heating, and subsequently set to obtain and maintain the target temperature.

This can be performed by a perfusion pump which has less mechanical impact on the physical integrity of the blood than a peristaltic pump.

In one embodiment according to the present invention, the whole-body hyperthermia system comprises means for bringing the patient under sedation or under anaesthesia.

For the purpose of the invention, the term "sedation" refers to the relaxed state of the patient, with or without loss of consciousness, after the administration of drugs. A patient under sedation can be synonymous for a patient under narcosis or under anaesthesia. The means for bringing the patient under sedation or under anaesthesia are provided to be supplied to the patient at a temperature $T_b$.

Specific embodiments refer to complete narcosis with no breathing. This has the advantage that heat loss via transpiration or via breathing is avoided.

Hereby the necessary oxygen supply for the body is provided by extracorporeal oxygenation of the blood. This is especially advantageous when blood is heated via an extracorporeal circuit.

In one embodiment according to the present invention, the whole-body hyperthermia system comprises means to supply oxygen to the patient. For the purpose of the invention, the term "oxygen" refers to any oxygen-containing gas that can be administered to a patient under sedation.

The oxygen supplying means are provided to supply oxygen to the patient at a temperature $T_b$. Advantageously, it has been found that the monitored body temperature $T_m$ reaches the predetermined target temperature $T_b$ at a faster pace. Furthermore, it has been found that supplying oxygen at the temperature $T_b$, allows the monitored body temperature $T_m$ to stabilize in a simple way at or close to $T_b$.

Upon complete narcosis spontaneous breathing stops and oxygen is supplied via a mask. Typically, the temperature of the applied gas is adapted to avoid heat losses by introduction of cold gasses.

When an extracorporeal system is used to heat the blood of an individual, oxygen can be supplied to the blood of the patient, which allows to reduce of replace oxygen supply by a breathing apparatus.

In one embodiment according to the present invention, the whole-body hyperthermia system is arranged to raise the patient's body temperature to the target temperature $T_b$ for at least a period of time $t_p$. The period of time $t_p$ is at least 6 h, typically at least 12 hours 12 h, preferably at least 14 h, more preferably at least 16 h, even more preferably at least 18 h, more preferably at least 20 h, even more preferably at least 22 h, and most preferably at least 24 h.

The systems and methods of the present invention rely on an interaction of a network of temperature sensors, and a network of heat fluxes sensors for raising and maintaining the hyperthermic conditions in an individual. Controllers receive signals from the various sensors and steer the various devices, via feedback systems.

The main heat flux to the individual is provided via heating of the blood, with extracorporeal heating and/or internally via intravenous catheter.

Other heat fluxes comprise:

The heating of the environment of the individual by temperature controlled air, fluids or gels. Compared to gels or fluids, the direct access to the skin has the advantage that the skin can be easily monitored and heated and isolated to prevent or counter heat loss. Local application of warm air or infrared radiation allows to heat those portions of the body with predominant. In addition to air, the individual might be placed on a heated table whereby typically temperature sensors are placed between the table and the body. The table is arranged to allow heating at specific parts of the table.

The heating of oxygen comprising gasses during mechanic breathing. As indicated above, this can be partially or completely replaced by oxygen supply directly to the blood.

The heating of fluids supplied to the individual such as nutrients, liquids for hydration, liquids with medicaments, or liquids with anaesthetics.

The minimisation of heat losses by using isolated tubing with short length and from material with low heat capacity or by heating the air of the cabinet in which the patient is located.

Temperature sensors and heat flux sensors provide signals to controllers that can adjust the amount of heat that is transported to the patient. This can be done by adjusting the temperature of the liquids and gasses, but can also be achieved by adapting the flow rate of liquids and gasses.

Temperature sensing can be on the body by measuring the temperature within the body or at the outside of the body. Temperature sensing can be remote via heat sensitive cameras. Heat sensing can also be indirect by measuring the temperature of the air in the cabinet surrounding the patient, the temperature of the blood in an extracorporeal system when it leaves the body, the temperature of exhaled air, the temperature of urine.

The controllers typically act via feedback mechanisms using proportional-integral-derivative (PID) regulation to prevent overshooting to undesired and unacceptable temperatures.

Each device providing heat to the individual can have its own controller. Alternatively, a plurality of controllers or all controllers can be incorporated in one dedicated controller device.

The coordinated operation of the elements of the system allow a fast heating of the individual without overshooting and allow to maintain a desired temperature which is accurate over time and homogenous for the entire body.

In typical embodiments, the systems and methods of the present invention, the individual is placed in a sarcophagus like cabinet wherein all heating elements and controllers are outside the cabinet whereby the different liquids and gasses are provided to the individual via tubing. Alternatively, one or more heating elements are placed within the cabinet to shorten the distance between heated medium and the patient. This still allows to have parts of the system outside the cabinet. For examples gas bottles with air or oxygen air are placed outside the cabinet. "Cold" gas subsequently enters the cabinet where it is heated close to the individual.

In order to prevent dehydration of the body via the skin the cabinet can contain a sensor to monitor the humidity of the ambient air. Humidity can be adjusted by e.g. evaporating water in the cabinet, or by humidifying the gasses (air or oxygen) which enter the cabinet. The foil wrapped around the body is not only a means of heat isolation but can also be a means to prevent or reduce dehydration through the skin.

Other embodiments make use of larger cabinets, e.g. when the individual is placed in a bath with fluid, or specific larger apparatus is needed within the cabinet.

Advantageously, it has been found that the whole-body hyperthermia system according to the invention can be used for treating an individual who can benefit from a long term (i.e. at least 6 hours) hyperthermia treatment. As explained before, such treatment is beneficial for cancer since tumour cells are more sensitive for high temperatures. The method is also applicable for the treatment of diseases wherein under normal condition fever occurs. Accordingly, the method is also applicable to bacterial and viral infections. For example, the method can be used in the treatment of antibiotic resistant bacteria, or of viruses for which no, or no effective antiviral compound have been developed.

In one embodiment according to the present invention, the whole-body hyperthermia system is further provided with means for administering additional compounds to the individual. Non-limitative examples of the additional compounds include transfused blood, nutritional compounds such as salt solutions. Preferably, the means are arranged to administer chemotherapeutic compounds. The means for administering additional compounds are arranged so that the additional compounds are administered at a temperature $T_b$.

In the methods of the present invention different sensors and different types of tubing are used to maintain and adjust the hyperthermic condition and to monitor and control functioning of the body.

To facilitate the operation of the system of the present invention it is advantageous to provide a kit comprising tubing for a fluid circuit for blood supply to the patient and comprising sensors and wiring to monitor the temperature or heat loss from the patient.

A typical fluid circuit for arterial blood supply and venous blood drain, is an access device with 2 separate lumen (cannula) or a double lumen access device also called catheter. The fluid circuit is optionally foreseen with one or more selected from the group consisting of a blood pressure sensor, optical blood sensor, temperature sensor, air bubble monitor, air bubble trap, gas and or fluid flow meter [e.g. velocity], gas flow filter, oxygen supply, oxygen saturation meter, heparin and or other fluid/gas access points, membrane oxygenator, heat exchanger.

Optionally the fluid circuit is isolated against heat loss or blood degradation to prevent exposure to light.

In addition to the fluid circuit for arterial blood supply and venous blood drain, the kit contains one or more of a temperature sensor, a heat flux sensor, a sensor for measuring respiratory activity, a sensor for measuring cardiac activity.

The fluid circuit also allows to analyse blood inline within the fluid circuit or to withdraw blood for analysis. Parameters which can be determined are for example pH, salts, haematocrit values, content of oxygen and other gasses.

The disposable to be conceived in a 'cassette' like (pre-wired) form factor for easy handling and mounting on the device reducing the risk for confusion and/or wrong connections.

Additionally, the disposable can be foreseen with an insolation/isolation foil or suit for the patient. Additionally, the disposable can be foreseen with a hat-like cover to connect to a cooling device especially to cool the patient's brain.

The kit can further contain means for cooling a selected part of the individual's body, said selected part being typically an individual organ. Said means for cooling an individual organ are typically a disposable means.

As mentioned hereabove, whereas the overall body temperature can be raised to a certain target temperature $T_b$, the target temperature being preferably in the range of 41.5° C. to 42.0 C°, some parts of the body risk suffering damage at such a temperature and have to be maintained at a temperature that is lower than the target temperature $T_b$. In order to avoid damage, the temperature of the brain cannot exceed 41.8° C., therefore the temperature is preferably 41.5° C., more preferably 41° C.

Other organs for which a different, preferably lower temperature may have to be targeted in order to avoid damage to the organs include the liver, the kidneys and the colon.

Said means for cooling individual organs can be provided on the skin of the individual, nearby the location of the organ, providing cooling via a heat flux through the skin. The brain can for example be cooled by applying a cooling cap, a cooling garment or a cooling pack around the head of the individual. Fluid is preferably circulated in or through the cooling cap, the ingoing fluid having preferably the temperature which is at most the temperature that is targeted for the brain.

Alternatively, said means for cooling individual organs may be applied on the surface of the organ itself, typically by use of minimally invasive or keyhole surgery. The organ is then cooled via an inflow/outflow of a cooling liquid. Said means for cooling individual organs is preferably placed in contact with the organ or wrapped at least partially around it with the active cooling side oriented towards the organ itself.

For maintaining the liver below a certain threshold temperature, gas-based anaesthesia may be used, resulting in a reduced activity and a slower metabolism of the liver.

Said means for cooling individual organs may be applied to the liver.

Said means for cooling individual organs may be applied to the kidneys.

Said means for cooling individual organs may be applied to the colon.

According to certain embodiments, said means for cooling individual organs are typically controlled by use of an organ based thermal model, having the purpose of continuously monitoring and adjusting the overall temperature of each of said organs individually.

The whole-body hyperthermia system is also useful for the treatment of collagen vascular diseases such as arthritis and psoriasis and for treating hypothermia.

Furthermore, when the system is used for hyperthermia treatment of cancer patients, it has been unexpectedly found that the rate of the temperature increase of the patient's body influences the annihilation mechanism of malign tumour cells. A fast heating rate promotes tumour cell destruction via cell necrosis, whereas a slower heating rate promotes cell destruction via apoptosis.

Since the hyperthermic conditions strongly decrease the viability of tumour cells, these cells become more susceptible to anticancer drugs, or irradiation. Lower doses of drugs or irradiation decrease side effects of these therapies.

Furthermore, the heating of the whole body not only has an effect on the primary tumour, localised in an organ of the body, but also on eventual circulating cells.

After heating, i.e. after the patient's body temperature has achieved the predetermined target temperature $T_b$, the first thermal means can be in principle removed from the patient and the temperature can be maintained by the second thermal means, and the patient can be wrapped in or covered by a heat barrier, such as a blanket, in accordance with procedures well known in the art.

In alternative embodiments one thermal means is used which first heats the individual to a desired temperature and afterwards maintains the patient at the desired temperature.

EXAMPLES

Example 1. In Vitro Model for Optimization of the First Means for Heating

A fibroblast cell line (Normal Human Dermal Fibroblasts (NHDF) and a tumour cell line are incubated in DMEM with fetal calf serum in an incubator with 5% CO2. Suitable cell lines are for example Hela cells, HT-1080 (connective tissue celline with activated N-ras oncogene), A375 (malignant skin melanoma cell line), and A549 (adenocarcinomic human alveolar basal epithelial cells).

Cells are placed in the incubator at 37° C., whereupon the temperature is raised to 41.5° C. over a time period ranging from 30 minutes to 4 hours. The volume of the medium on the cells is kept to a minimum to avoid delay in the heating.

Cells viability is determined and apoptosis and necrosis of cells is measured.

The experiment allows to determine the effect of a shallow or steep increase of the temperature as achieved by the first means when applied on the body.

Example 2. In Vitro Model for Determining Efficiency and Specificity

The above described cells are incubated for different time periods (4, 6, 8, 12, 16, 20, 24, 36 hours) at different temperatures (37, 39, 40, 40.5, 41, 41.5 and 42° C.).

Cells viability is determined and apoptosis and necrosis of cells is measured.

The experiment allows determining the efficiency of the method (% killed tumour cells) and the specificity (% killed tumour cells versus killed normal cells).

The above system can be further used to mimic conditions in tumour tissue (hypoxia, pH) and to determine the effect on cells which have been irradiated or treated with cancer medicaments.

Example 3. In Vivo Model for Long Term Hyperthermia

Mice with a tumour are placed under anaesthetics on a heated plate in a heated cabinet. For small laboratory animals the heat transfer is sufficient enough to provide a whole body hyperthermia without the application of first and second means as described in the specification.

Mice are killed and tumour tissue is examined for cell death.

The animal model allows comparing cell death as obtained in example 2 and in the mouse model using the same time period and the same temperature.

The invention claimed is:

1. A whole-body hyperthermia system for raising the body temperature of the entire body of an individual to a predetermined target temperature Tb and for stabilizing said body temperature at said target temperature Tb, said system comprising:
a cabinet, in which the individual is located, said cabinet being provided with isolation and heating for heating the air of the cabinet, for maintaining an individual at an elevated temperature,
at least one thermal means, configured to raise said body temperature at a rate of at least 1° C./hour, and subsequently set to obtain and maintain the target temperature Tb of said individual,
wherein said at least one thermal means comprises a first thermal means for raising said body temperature at a rate of at least 1° C./hour,
wherein raising said body temperature by said first thermal means is not performed by external heating of the blood system and
wherein said first thermal means do not comprise an internally heated fluid circuit,
one or more devices to prevent or counter heat loss from the individual, said one or more devices being devices for heating liquids being introduced in the body, said liquids comprising one or more of nutrients, liquids for hydration, liquids with medicaments, and liquids with anaesthetics,
one or more sensors monitoring the temperature or heat flux of the individual, connected to controllers steering said devices to prevent or counter heat loss and steering the at least one thermal means,
wherein said first thermal means has at least a first portion and at least a second portion, wherein the at least first portion of the first thermal means is arranged to raise the body temperature of at least a first series of body parts of the individual to the target temperature $T_b$, and
wherein the at least second portion of the first thermal means is arranged to prevent at least a second series of body parts to exceed a target temperature $T_s$,
wherein the temperature $T_s$ is lower than the temperature $T_b$,
wherein said second portion further includes means for cooling individual organs,
wherein said means for cooling individual organs are applied to the brain and at least one of the liver, the kidneys and the colon, and in that, said system further comprises means for bringing the individual under anaesthesia.

2. The system according to claim 1, wherein the one or more sensors monitoring the temperature of the individual comprise one or more of sensors measuring the temperature internally, sensors measuring the temperature externally and contacting the skin, and sensors measuring the temperature externally and not contacting the skin.

3. The system according to claim 1, wherein said at least one thermal means further comprises at least a second thermal means for further adjusting the body temperature to said target temperature Tb,
wherein said second thermal means comprise a fluid circuit, which is at least partially within the individual,
wherein a fluid, heated by a heat exchanger to a set temperature Tf, is circulated through said fluid circuit, wherein Tf is Tb+/−0.5° C.

4. The whole-body hyperthermia system according to claim 3, wherein said first and said second thermal means are different from each other.

5. The whole-body hyperthermia system according to claim 3, wherein said fluid circuit of the second thermal means is an internally heated catheter.

6. The whole-body hyperthermia system according to claim 1, wherein said system is provided with means for monitoring the body temperature and vital signs of the individual, such as respiratory activity, cardiac activity and blood parameters.

7. The whole-body hyperthermia system according to claim 1, wherein said system is provided with means to administer additional compounds to the individual, such as transfused blood, chemotherapeutic drugs and/or nutritional compounds, such as salt solutions, and wherein said additional compounds are administered at a temperature Tb, and/or wherein said system is provided with one or more isolation elements for an individual, such as isolation foil or suit for torso or limbs, or a helmet or cap like device for application on the head.

8. The system according to claim 1, wherein said means for cooling individual organs are provided on the skin of the individual nearby the location of the organ, configured to provide cooling through the skin, or are applied on the surface of the organ itself by use of minimally invasive or keyhole surgery.

9. The system according to claim 1, wherein said means for cooling individual organs are a disposable means.

10. A disposable kit for use in the system according to claim 1, wherein said disposable kit comprises tubing for a fluid circuit for blood supply to an individual and comprises sensors to monitor the temperature or heat loss from the patient.

* * * * *